United States Patent [19]
Ikeda et al.

[11] Patent Number: 5,510,536
[45] Date of Patent: Apr. 23, 1996

[54] PRODUCTION METHOD OF TRIS(PENTAFLUOROPHENYL)BORANE USING PENTAFLUOROPHENYLMAGNESIUM DERIVATIVES PREPARED FROM PENTAFLUOROBENZENE

[75] Inventors: Yoshihiko Ikeda, Shinnanyo; Takeo Yamane, Ogori; Eiichi Kaji; Kenji Ishimaru, both of Shinnanyo, all of Japan

[73] Assignee: Tosoh Akzo Corporation, Tokyo, Japan

[21] Appl. No.: 171,639

[22] Filed: Dec. 22, 1993

[30] Foreign Application Priority Data

Dec. 28, 1992 [JP] Japan .................................. 4-361474

[51] Int. Cl.⁶ ..................................................... C07F 5/00
[52] U.S. Cl. ........................................................... 568/6
[58] Field of Search ...................................... 568/6

[56] References Cited

U.S. PATENT DOCUMENTS 2,853,525  9/1958  Wittig et al. .

FOREIGN PATENT DOCUMENTS 2072058  12/1992  Canada .

OTHER PUBLICATIONS

March et al., "Advanced Organic Chemistry", 2nd Ed. (1977) McGraw–Hill Book Co., N.Y., N.Y., pp. 564–565.
Cohen et al., Adv. Fluorine Chemistry, 6, pp. 119–121 (1970).
Yang et al., JACS (1991), 113, 3623–3625.
CA 59: 8771 b, Chem. Abstract, Massey et al. (Proc. Chem. Soc., 1963 (Jul.), 212).
Chemical Abstracts, vol. 100, No. 17, Apr. 23, 1984, AN 139179s, Hiroshi Kobayashi, et al., "Synthesis of Trifluoromethylated Tetraphenylborates and the Solvent–Extraction Properties of Their Ion–Associates with Alkali–Metal Ions. Application of Tetraarylborates to Separation Analysis of Univalent Cations".
The Journal of Organic Chemistry, vol. 29, 1964, pp. 2385–2389, Robert J. Harper, et al., "Reactions of Organometallics with Fluoroaromatic Compounds".

*Primary Examiner*—Joseph Paul Brust
*Attorney, Agent, or Firm*—Oblon, Spivak, McClelland, Maier & Neustadt

[57] ABSTRACT

A method of producing tris(pentafluorophenyl)borane or its ether complex, using pentafluorobenzene as the source of the pentafluorophenyl group. The process comprises reacting pentafluorobenzene with an organo metallic compound (II) of the formula $R_{2-n}MgX_n$, wherein n denotes a real number of 0 or 1, X denotes a halogen atom and R denotes a hydrocarbon group of 1 to 10 carbon atoms. The reaction is carried out in an ether solvent at a temperature not less than 25° C. The resulting pentafluorophenylmagnesium compound has the formula $(C_6F_5)_{2-n}MgX_n$ (III), wherein n denotes a real number of 0 or 1 and X denotes a halogen atom. The pentafluorophenylmagnesium compound of the formula (III) is next reacted with a borane compound of the formula $BX_3$, wherein X denotes a halogen atom. The reaction is carried out at a temperature in the range of 0° C. to 250° C., preferably 60° C. to 250° C. in an ether solvent such as tetrahydrofurane or diethyl ether, or in a non-aqueous mixture of ether solvent and hydrocarbon solvent. The ether solvent forms a complex coordinated to tris(pentafluorophenyl)borane. The complexed solvent is eliminated by either direct or indirect eliminating processes. The product may then be reacted with 1:1 equivalents of pentafluorophenyllithium to prepare tetrakis (pentafluorophenyl)borate and subsequently mixed with a solution of N,N-dimethylanilinium to produce N,N-dimethylanilinium tetrakis(pentafluorophenyl)borate crystals. The final product is very pure with purities exceeding 98 wt. %. The anilinium product is usable as an auxiliary catalyst for cationic complex polymerization.

6 Claims, No Drawings

PRODUCTION METHOD OF TRIS(PENTAFLUOROPHENYL)BORANE USING PENTAFLUOROPHENYLMAGNESIUM DERIVATIVES PREPARED FROM PENTAFLUOROBENZENE

BACKGROUND OF THE INVENTION

The present invention relates to a novel production method of tris(pentafluorophenyl)borane using pentafluorobenzene as its starting material. The boron derivatives obtainable by the invention are extremely serviceable compounds as an auxiliary catalyst for cationic complex polymerization, and also as intermediates of N,N-dimethylauilinium tetrakis(pentafluorophenyl)borate which is useful as an auxiliary catalyst for cationic complex polymerization.

In recent years, scientific literatures or patents for conducting polymerization reactions using these compounds and organometallic complexes have increased remarkably; e.g. J. Am. Chem. Soc., 113, 3626 (1991), Macromol. Chem. Rapid Commun., 2, p. p. 663–667 (1991) or the like. However, for the production of tris(pentafluorophenyl)borane, relatively expensive bromopentafluorobenzene has been used conventionally as a starting material for the source of pentafluorophenyl group.

The method was such that bromopentafluorobenzene was subject to a bromine-metal exchange reaction at a low temperature of −70° C. using organometallic compounds such as butyllithium to generate pentafluorophenyllithium (J. Org. Chem., 29, 2385 (1964), J. Org. Chem., 31, 4229 (1966) and Synthesis of Fluoroorganic Compounds, p. 190, Springer-Verlag (1985)), which was reacted with boron trichloride, boron trifluoride or the like as a starting raw material for the boron source, or bromopentafluorobenzene was reacted with magnesium to generate Grignard's reagent such as pentafluorophenylmagnesium bromide (J. Chem. Soc. 166 (1959), Z. Naturforschg., 20b, 5 (1965) and Synthesis of Fluoroorganic Compounds, p. 141, Springer-Verlag (1985) etc.), which was reacted similarly with boron trichloride, boron trifluoride or the like as a starting raw material for the boron source, thereby producing tris(pentafluorophenyl)borane (J. Organometallic Chem., 2, 245–250 (1964)).

Bromopentafluorobenzene can be obtained by brominating pentafluorobenzene. However, if it would be possible to produce tris(pentafluorophenyl)borane directly from pentafluorobenzene, the production processes could be reduced by one process leading to easier availability and also lower price of starting raw material. On the other hand, literatures for generating pentafluorophenylmagnesium bromide for the reaction using pentafluorobenzene as a starting raw material have already been published (J. Chem. Soc., 166 (1959), Synthesis of Fluoroorganic Compounds p141, J. Org. Chem., 29, 2385 (1964) and ibid, 31, 4229 (1966), but the production of tris(pentafluorophenyl)borane has been unknown.

In view of the situation aforementioned, the inventors have so extensively investigated that the brominating process of pentafluorobenzene may be eliminated by changing the use of bromopentafluorobenzene, which has been used as a starting material for the production of tris(pentafluorophenyl)borane, to that of pentafluorobenzene, further the cost for the production installation may be decreased by making the very low temperature such as −70° C. at the time of generating pentafluorophenyllithium from bromopentafluorobenzene to be unnecessary, and further the use of relatively expensive reacting agent such as organolithium compound may be omitted, thus leading to the present invention.

SUMMARY OF THE INVENTION

Namely, the gist of the invention relates to a production method of tris(pentafluorophenyl)borane or a complex coordinating an ether type solvent to tris(pentafluorophenyl)borane characterized in that pentafluorophenylmagnesium derivatives having a following general formula $(C_6F_5)_{2-n}MgX_n$ (wherein n denotes a real number of 0 or 1 and X denotes a halogen atom) are made to be generated at a temperature of 0° to 250° C. from pentafluorobenzene, and this is used as a source of pentafluorophenyl group.

Briefly our invention is a method of producing tris(pentafluorophenyl)borane employing a pentafluorophenyl magnesium derivative prepared from pentafluorobenzene. The process is characterized in that pentafluorobenzene of the formula (I)

$$C_6F_5H \qquad (I)$$

is mixed with 0.5–1.5 equivalents of organometallic compound of the formula (II)

$$R_{2-n}MgX_n \qquad (II),$$

wherein n denotes a real number of 0 or 1, X denotes a halogen atom and R denotes a hydrocarbon group of 1 to 10 carbon atoms which may include a functional group having no influence on the reaction, in an ether solvent or in a non-aqueous mixture of ether solvent and hydrocarbon solvent, within a temperature range of −40° to 250° C. Preferably, the mixture is allowed to react at a temperature of not less than 25° C. resulting in the preparation of a pentafluorophenyl magnesium compound of the formula (III)

$$(C_6F_5)_{2-n}MgX_n \qquad (III),$$

wherein n denotes a real number of 0 or 1, and X denotes a halogen atom. Next, the pentafluorophenyl magnesium compound of the formula (III) is reacted with a boron compound of the formula (IV)

$$BX_3 \qquad (IV),$$

wherein X denotes a halogen atom or a substituent represented by the following formula (V)

$$OR \qquad (V),$$

wherein R denotes a hydrocarbon group of 1 to 10 carbon atoms which may include a functional group having no influence on the reaction, or a substituent represented by the formula (VI)

$$NRR' \qquad (VI),$$

wherein R and R' denote a hydrocarbon group of 1 to 20 carbon atoms, each of which may include a functional group having no influence on the reaction, or R and R' may combine with each other to form a ring. The boron compound (IV) may form a complex of 1:1 to an ether solvent in a ratio of 1. The boron compound (IV) and pentafluorophenylmagnesium compound III are combined in a ratio of 1 equivalent of the boron compound to 2.1–3.9 equivalents of the pentafluorophenylmagnesium compound. The temperature range of the reaction may be from 0° C. to 250° C. and the resulting product is tris(pentafluorophenyl)borane of the formula (VII)

(C₆F₅)₃B  (VII), or a complex coordinating an ether solvent to the tris(pentafluorophenyl)borane.

DETAILED DESCRIPTION OF THE INVENTION

In following, the invention will be illustrated in details.

The ether type solvents referred so in the invention indicate diethyl ether, dipropyl ether, diisopropyl ether, dibutyl ether, diisoamyl ether, 1,2-dimethoxyethane, 1,2-diethoxyethane, di-2-methoxyethyl ether, tetrahydrofuran, tetrahydropyran, 1,4-dioxane, etc.

Next, the hydrocarbon type solvents referred so in the invention indicate saturated hydrocarbons such as pentane, isopentane, hexane, cyclohexane, heptane, octane, nonane, decane, undecane, dodecane, tridecane, tetradecane, pentdecane, hexadecane, n-paraffin or petroleum ether etc., aromatic hydrocarbons such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene or butylbenzene, etc. and mixtures thereof.

Next, the functional groups having no influence on the reaction in the formula [II] referred so in the invention indicate methyl group, ethyl group, propyl group, isopropyl group, propenyl group, 2-isopropenyl group, allyl group, butyl group, sec-butyl group, tert-butyl group, isobutyl group, pentyl group, sec-pentyl group, tert-pentyl group, neo-pentyl group, sec-isopentyl group, hexyl group, sec-hexyl group, isohexyl group, sec-isohexyl group, cyclohexyl group, phenyl group, benzyl group, o-tolyl group, m-tolyl group, p-tolyl group, methoxymethyl group, methylthiomethyl group, 2-dimethylaminoethyl group, o-anisyl group, m-anisyl group, m-anisyl group, p-anisyl, group, trimethylsilylmethyl group, etc., and the examples of organomagnesium compounds represented by the formula [II] include methylmagnesium iodide, methylmagnesium bromide, methylmagnesium chloride, dimethylmagnesium, ethylmagnesium bromide, ethyl magnesium chloride, ethylmagnesium iodide, diethylmagnesium, propylmagnesium bromide, propylmagnesium chloride, butylmagnesium bromide, butylmagnesium chloride, sec-butylmagnesium bromide, sec-butylmagnesium chloride, tert-butylmagnesium bromide, tert-butylmagnesium chloride, isobutylmagnesium bromide, isobutylmagnesium chloride, hexylmagnesium bromide, hexylmagnesium chloride, cyclohexyl magnesium bromide, cyclohexylmagnesium chloride, ethylbutylmagnesium, dibutylmagnesium, etc.

Next, Rs in the substituent represented by the formula [V] referred so in the invention include, for example, methyl group, ethyl group, propyl group, isopropyl group, propenyl group, isopropenyl group, allyl group, butyl group, sec-butyl group, tert-butyl group, isobutyl group, pentyl group, sec-pentyl group, hexyl group, cyclohexyl group, octyl group, decyl group, phenyl group, benzyl group, methoxymethyl group, methylthiomethyl group, 2-methoxyethyl group, acetyl group, benzoyl group, trimethylsilyl group, etc.

Next, Rs in the substituent represented by the formula [VI] referred so in the invention include, for example, methyl group, ethyl group, propyl group, isopropyl group, propenyl group, 2-isopropenyl group, allyl group, butyl group, sec-butyl group, tert-butyl group, isobutyl group, pentyl group, sec-pentyl group, hexyl group, cyclohexyl group, octyl group, decyl group, phenyl group, benzyl group, methoxymethyl group, methylthiomethyl group, 2-dimethoxyethyl group, o-anisyl group, m-anisyl group, p-anisyl group, acetyl group, benzoyl group, trimethylsilyl group, tetramethylene group, pentamethylene group, N-methyl-3-azapentamethylene group, 3-oxapentamethylene group or 3-thiapentamethylene group, etc.

From above, as the examples of boron compounds represented by the formula [IV] referred so in the invention, boron trifluoride, boron trichloride, boron tribromide, boron triiodide, trimethyl borate, triethyl borate, tripropyl borate, triisopropyl borate, tributyl borate, trimethyleneborate, tris-(dimethylamino)borane, tris(diethylamino)borane, tripyrrolidinoborane, tripieridinoborane or trimorpholinoborane etc. are exemplified. Further, complexes such as boron trifluoride-diethyl ether complex, boron trifluoride-dimethyl sulfide complex, boron trichloride-diethyl ether complex, boron trichloride-dibutyl ether complex, etc. are also included in this category.

Concrete method for the production will be illustrated in sequence below. The method of generating pentafluorophenylmagnesium derivatives represented by the formula [III] is as follows: To one equivalent of pentafluorobenzene represented by the formula [I] is admixed 0.5 to 1.5 equivalents of organomagnesium compound represented by the formula [II] within a range of −40°~250° C. and thereafter the mixture is subject to reaction within a range of 25°~250° C. In this reaction, if the organomagnesium compound represented by the formula [II] is used in too excess amount to pentafluorobenzene represented by the formula [I] , unreacted organomagnesium compound represented by the formula [II] may remain in large quantities to produce much impurities, while if used in too less amount, pentafluorobenzene becomes useless. Hence, it is desirable to use 0.8~1.2 equivalents of organomagnesium compound represented by the formula [II]. If the reaction temperature is too lower than 25° C., the progress of reaction becomes extremely slow while if too higher than 200° C., the progress of side reaction becomes extremely fast, resulting in very low yield in both cases, hence it is desirable to react within a range from 25° C. to 200° C. By reacting the reaction mixture for 0.5 to 70 hours at the same temperature, pentafluorophenylmagnesium derivatives represented by the formula [III] are prepared. The example of pentafluorophenylmagnesium derivatives produced here represented by the formula [III] are such as C₆F₅MgCl, C₆F₅MgBr, C₆F₅MgI, (C₆F₅)₂Mg, C₆F₅MgET or C₆F₅MgBu.

Following this, to one equivalent of boron compound represented by the formula [IV], 2.1 to 3.9 equivalent of pentafluorophenylmagnesium derivatives represented by the formula [III] prepared by aforesaid method are mixed within a range from 0° C. to 250° C. This reaction is desirable however to react within a range from 25° C. to 200° C. when a great deal of pentafluoromagnesium derivatives is remaining in the initial stage, since, if the reaction temperature is lower than 25° C., then the reaction velocity decreases remarkably taking a long time for reaction and, if it is higher than 200° C., then pentafluoromagnesium derivatives are in fear of decomposition.

In addition, if the number of equivalent of pentafluoromagnesium derivatives used is too lower than 2.1 equivalent, the yield will decrease conspicuously and, if it is too much than 3.9 equivalents, the decrease of yield will result due to the production of tetrakis (pentafluorophenyl) borate.

Hence, if considering the economy, use of 2.5 to 3.5 equivalents may be desirable. By reacting the reaction mixture for 0.5 to 50 hours within a range from 0° C. to 250° C., tris(pentafluorophenyl)borane represented by the formula [VII] or a complex coordinating an ether type solvent to tris(pentafluorophenyl)borane can be produced. At that time, it is desirable that the reaction temperature is elevated within a range from 60° C. to 250° C. and the reaction is continued for 0.5 to 50 hours, thus enabling the reaction to be completed.

This is because of that, in this case, fluorobis(pentafluorophenyl)borane and tetrakis(pentafluorophenyl)borate derivatives or complexes coordinating an ether type solvent thereto are produced as by-products, which is hence converted to complex of tris(pentafluorophenyl)borane through the disproportionation, and therefore, if under 60° C., the reaction velocity will become extremely slow and, if over 200° C., the decomposition of product occurs.

The ether type solvent coordinated to tris(pentafluorophenyl)borane can be eliminated by a direct eliminating method or an indirect eliminating method. The direct eliminating method referred so here is a method wherein the complex coordinating an ether type solvent to tris(pentafluorophenyl)borane is evaporated with sublimation at 30° C. to 200° C. at or under 10 Torr, desirably at or under 1 Torr, after the solvent is distilled off.

Next, the indirect eliminating method referred so here includes two methods; (1) a method wherein not less than 1 equivalent of alkylaluminum to the solvent, which is coordinated to tris(pentafluorophenyl)borane, is reacted to coordinate that solvent to the used alkylaluminum, thereby eliminating the solvent and (2) a method wherein a hydrocarbon type solvent having a higher boiling point than said coordinated solvent is mixed and this hydrocarbon type solvent is distilled off, thereby eliminating the coordinated solvent azeotropically.

When eliminating the coordinated solvent by the method (2), by using the hydrocarbon type solvent and heating up to 60° C. to 200° C., difluoropentafluorophenylborane or fluorobis(pentafluorophenyl)borane and halogenated magnesiumtetrakis(pentafluorophenyl)borate or their complexes coordinating the ether type solvent thereto undergo disproportionation, thus elevating the yield of product.

Hence, the hydrocarbon type solvent to be used for the azeotropic elimination is desirable to have a boiling point of 60° to 200° C. Since, in the case of saturated hydrocarbons, the solubility of tris(pentafluorophenyl)borane produced, represented by the formula [VIII], is low, when producing it by crystallization after eliminating the coordinated ether type solvents, it is desirable to use hexane, heptane, octane, nonane, decane, undecane, dodecane, tridecane, or their mixture etc., and, since, in the case of aromatic hydrocarbons, the solubility of tris(pentafluorophenyl)borane or the complex coordinating solvent to tris(pentafluorophenyl)borane produced is relatively high inversely, when used as a solution, it is desirable to use benzene, toluene, o-xylene, m-xylene, p-xylene, ethylbenzene, propylbenzene, etc.

The invention has a very large industrial value in the points that a method of producing tris(pentafluorophenyl)borane or a complex coordinating the ether type solvent to tris(pentafluorophenyl)borane being extremely important compounds as an auxiliary catalyst for cationic polymerization by shortening the production processes by one process by changing the starting material from expensive bromopentafluorobenzene to pentafluorobenzene can be provided at low cost and furthermore capacity as an auxiliary catalyst can be drawn out completely by eliminating the coordinated ether type solvent.

In the following, the invention will be illustrated in more detail using the examples, but this invention is subject to no restrictions by the following examples so long as it does not exceed the gist.

The reaction yield is a value wherein the produced tris(pentafluorophenyl)borane or the complex coordinating ether type solvent to the tris(pentafluorophenyl)borane is determined by $^{19}$F-NMR using pentafluorotoluene as an internal standard, or after further subjected to a reaction with 1.1 equivalents of pentafluorophenyllithium, it is derived to N,N-dimethylanilinium tetrakis(pentafluorophenyl)borate through ion-exchanging to the cation by N,N-dimethylanilinium, which is determined by $^{19}$F-NMR using pentafluorotoluene as an internal standard.

EXAMPLE 1

To a solution of pentafluorobenzene (10.66 g, 63.5 mmol) in anhydrous tetrahydrofuran (20 ml, hereinafter THF) was added dropwise 25.5 wt. % ethylmagnesium bromide/diethyl ether solution (31.81 g, 60.9 mmol) under an inert atmosphere using dropping funnel while keeping the temperature of the reaction mixture at 25° to 35° C., and the mixture was stirred for 50 hours at the same temperature. Further, a solution of boron trifluoride (2.70 g, 19.0 mmol) in toluene (50 ml) was added dropwise using dropping funnel while keeping the temperature of the reaction mixture at 25° to 40° C. After the completion of dropwise addition, the reaction mixture was instantly heated and was stirred with heating for about 5 hours while keeping the temperature of the reaction mixture at 70° C. The reaction mixture was collected and the yield of obtained tris(pentafluorophenyl)borane was measured through $^{19}$F-NMR using pentafluorotoluene as an internal standard to obtain tetrahydrofuran complex of tris(pentafluorophenyl)borane in 91%.

To the obtained solution of tris(pentafluorophenyl)borane in tetrahydrofuran was added toluene (100 ml), than the mixture was heated up to 110° C., tetrahydrofuran was distilled off, and magnesium salt was precipitated and filtered off, which was thereafter mixed with a separately prepared solution of pentafluorophenyllithium in diethyl ether at −70° C. Then, after the temperature of the reaction mixture was slowly elevated and reached 25° C., the reaction mixture was subjected to distilling off of the solvent and mixed with a solution of N,N-dimethylanilinium to give instantly a deposit of N,N-dimethylanilinium tetrakis(pentafluorophenyl)borate crystal. The obtained crystal was filtered, dissolved into diethyl ether and then was recrystallized with an addition of hexane, followed by drying, to give N,N-dimethlanilinium tetrakis(pentafluorophenyl)borate in 61% yield. On measuring the purity thereof using pentafluorotoluene as an internal standard, it was more than 98 wt. % purity.

EXAMPLE 2

To a solution of pentafluorobenzene (10.50 g, 62.5 mmol) in anhydrous 1,2-dimethoxyethane (40 ml) was added dropwise 18.1 wt. % ethylmagnesium bromide/1,2-dimethoxyethane solution (45.18 g, 61.4 mmol) under an inert atmosphere using a dropping funnel while keeping the temperature of the reaction mixture at 25° to 35° C., and the mixture was stirred for 65 hours at the same temperature. Further, after a solution of boron trifluoride-diethyl ether complex (2.70 g, 19.0 mmol) in ethylbenzene (50 ml) was added thereto dropwise using a dropping funnel while keeping the temperature of the reaction mixture at 25° to 40° C., it was stirred with heating for about 3 hours while keeping the reaction temperature at 85° C. The reaction mixture was collected and was subjected to measuring yield of the obtained tris(pentafluorophenyl)borane using pentafluorotoluene as an internal standard to give 1,2-dimethoxyethane complex of tris(pentafluorophenyl)borane in 94%.

EXAMPLE 3

To a solution of pentafluorobenzene (11.01 g, 65.5 mmol) in anhydrous diethyl ether (20 ml) was added dropwise 25.5 wt. % ethylmagnesium bromide/diethyl ether solution (32.29 g, 61.8 mmol) under an inert atmosphere using a dropping funnel while keeping the temperature of the reaction mixture at 25° to 35° C., and the mixture was stirred for 72 hours under reflux with heating. Further, a solution of boron trifluoride-diethyl ether complex (2.74 g, 19.3 mmol) in octane (50 m ml) was added dropwise using a dropping funnel while keeping the temperature of the reaction mixture at 25° to 40° C. and diethyl ether was distilled off by heating immediately after the completion of dropwise addition. While keeping the temperature of the reaction mixture at 150° C., it was stirred with heating for about 5 hours until it becomes a suspension by crystallizing the side-produced magnesium fluoride bromide. After a removal of magnesium fluoride bromide from the obtained suspension by filtration, the obtained octane solution of tris(pentafluorophenyl)borane was cooled down to 0° C. and the deposited white crystal was dried to give tris(pentafluorophenyl)borane in 65% yield.

EXAMPLE 4

To a solution of pentafluorobenzene (10.50 g, 62.5 mmol) in anhydrous tetrahydrofuran (40 ml) was added dropwise 18.1 wt. % butylmagnesium chloride/tetrahydrofuran solution (45.18 g, 61.4 mmol) under an inert atmosphere using a dropping funnel while keeping the temperature of the reaction mixture at 25° to 35° C., and the mixture was stirred for 5 hours at the same temperature. Further, a solution of boron trifluoride-diethyl ether complex (2.70 g, 19.0 mmol) in octane (50 ml) was added dropwise using a dropping funnel while keeping the temperature of the reaction mixture at 25° to 40° C. and tetrahydrofuran was distilled off by heating immediately after the completion of dropwise addition. While keeping the temperature of the reaction mixture at 110° C., it was heated for about 11 hours under stirring. On measuring the yield from the obtained solution through $^{19}$F-NMR using pentafluorotoluene as an internal standard, tetrahydrofuran complex of tris(pentafluorophenyl)borane was obtained in 93% yield.

EXAMPLE 5

To a solution of pentafluorobenzene (11.01 g, 65.5 mmol) in anhydrous 1,2-dimethoxyethane (20 ml) was added dropwise 25.5 wt. % butylethylmagnesium/heptane solution (32.29 g, 61.8 mmol) under an inert atmosphere using a dropping funnel while keeping the temperature of the reaction mixture at 25° to 35° C., and the mixture was stirred for 72 hours at the same temperature. Further, a solution of boron trifluoride-diethyl ether complex (2.74 g, 19.3 mmol) in octane (50 ml) was added dropwise using a dropping funnel while keeping the temperature of the reaction mixture at 25° to 40° C. and it was stirred with heating for 3 hours instantly after the completion of dropwise addition while keeping the temperature of the reaction mixture at 85° C. The reaction mixture was collected and, on measuring the yield of the obtained tris(pentafluorophenyl)borane through $^{19}$F-NMR using pentafluorotoluene as an internal standard, 1,2-dimethoxyethane complex of tris(pentafluorophenyl)borane was obtained in 94% yield.

After adding toluene (100 ml) to the obtained 1,2-dimethoxyethane solution of tris(pentafluorophenyl)borane, dimethoxyethane was distilled off by heating and magnesium salt was precipitated and filtered, which was thereafter mixed with a separately prepared diethyl-ether solution of pentafluorophenyllithium at −70° C. Then, after the temperature of reaction mixture was slowly elevated up to 25° C., the solvent is distilled off under a reduced pressure and it was mixed with an aqueous solution of N,N-dimethylanilinium chloride to give instantly a deposite of N,N-dimethylanilinium tetrakes(pentafluorophenyl)borate crystal. After the obtained crystal was filtered, dissolved into diethyl ether and recrystallized with an addition of hexane, followed by drying, N,N-dimethylanilinium tetrakis(pentafluorophenyl)borate was obtained in 58% yield. On measuring the purity thereof through $^{19}$F-NMR using pentafluorotoluene as an internal standard, it was more than 98 wt. %.

EXAMPLE 6

To a solution of pentafluorobenzene (11.01 g, 65.5 mmol) in anhydrous diethyl ether (20 ml) was added dropwise 25.5 wt. % ethylmagnesium bromide/diethyl ether solution (32.29 g, 61.8 mmol) under an inert atmosphere using a dropping funnel while keeping the temperature of reaction liquor at 25° to 40° C., and the mixture was stirred for 72 hours at 60° C. Further, after cooled, 1.0 mole/L solution of boron trichloride/hexane solution (19.3 mL, 19.3 mmol) in toluene (50 ml) was added dropwise using a dropping funnel while keeping the temperature of the reaction mixture at 25° to 40° C. Immediately after the completion of dropwise addition, it was heated and kept on stirring with heating for about 8 hours until it becomes a suspension by crystallizing the sideproduced magnesium fluoride chloride with maintaining the temperature of the reaction mixture at 110° C. After magnesium fluoride chloride was removed by filtration from the obtained reaction mixture, octane (30 ml) was added to the obtained toluene solution of tris(pentafluorophenyl)borane and toluene was distilled off at 70° C., 200 Torr., and then, after cooled and crystallized, tris(pentafluorophenyl)borane was obtained in 53% yield.

EXAMPLE 7

To a solution of pentafluorobenzene (11.01 g, 65.5 mmol) in anhydrous 1,2-dimethoxyethane (20 ml) was added dropwise 25.5 wt. % cyclohexylmagnesium bromide/1,2-dimethoxyethane solution (45.41 g, 61.8 mmol) under an inert atmosphere using a dropping funnel while keeping the temperature of reaction liquor at 25° to 35° C., and the mixture was stirred for 72 hours at 60° C. Further, after cooled, 1.0 mol/L boron trichloride/hexane solution (19.3 ml, 19.3 mmol) and decane (50 ml) solution were added dropwise using a dropping funnel while keeping the temperature of the reaction mixture at 25° to 40° C. Immediately after the completion of dropwise addition, it was heated and kept on stirring with heating for 3 hours while keeping the temperature of the reaction mixture at 85° C. After the reaction mixture was collected, 1,2-dimethoxyethane complex of tris(pentafluorophenyl)borane was obtained in 94% yield, on measuring the yield of the obtained tris(pentafluorophenyl)borane through $^{19}$F-NMR using pentafluorotoluene as an internal standard.

EXAMPLE 8

To a solution of pentafluorobenzene (11.01 g, 65.5 mmol) and anhydrous 1,2-dimethoxyethane (20 ml) was added 25.5 wt. % cyclohexylmagnesium bromide/1,2-dimethoxyethane solution (45.41 g, 61.8 mmol) under an inert atmosphere using a dropping funnel with maintaining the temperature of reaction mixture at 25° to 35° C., and was stirred for 72 hours at 60° C. After cooled, further trimethyl borate (2.01 g, 19.3 mmol) was dropwise added using a dropping funnel with maintaining the temperature of reaction mixture at 25° to 40° C. and, immediately after the completion of dropwise addition, it was heated and kept on stirring with heating for 3 hours with maintaining the temperature of reaction mixture at 85° C. After the reaction mixture was collected, 1,2-dimethoxyethane complex of tris(pentafluorophenyl)borane was obtained in 91% yield, on measuring the yield of obtained tris(pentafluorophenyl)borane through $^{19}$F-NMR using pentafluorotoluene as an internal standard.

EXAMPLE 9

To a solution of pentafluorobenzene (11.01 g, 65.5 mmol) and anhydrous diethyl ether (20 mL) was dropwise added 25.5 wt. % cyclohexylmagnesium bromide/diethyl ether solution (45.41 g, 61.8 mmol) under an inert atmosphere using a dropping funnel with maintaining the reaction temperature at 25°~35° C., and the mixture was stirred for 72 hours at 60° C. After cooled, further 1.0 mmol/L boron trichloride/hexane solution (19.3 mL, 19.3 mmol) was dropwise added using a dropping funnel with maintaining the temperature of reaction mixture at 25°~40° C. and, after the completion of said dropwise addition, toluene was added thereto. The reaction mixture was heated and kept on stirring with heating for about 5 hours until it becomes a suspension liquid by crystallizing the side-produced magnesium fluoride bromide while keeping the temperature of reaction temperature at 110° C. After magnesium fluoride chloride was removed by filtration from the obtained suspension, the obtained toluene solution of tris(pentafluorophenyl)borane was concentrated to drying up and subjected to sublimation under vacuum to give tris(pentafluorophenyl)borane in 71% yield. On measuring the purity of the obtained tris(pentafluorophenyl)borane through $^{19}$F-NMR using pentafluorotoluene as an internal standard, it was more than 95 wt. %.

What is claimed is:

1. A method of producing tris(pentafluorophenyl)borane comprising mixing pentafluorobenzene of the formula (I)

$$C_6F_5H \qquad (I)$$

with 0.5–1.5 equivalents of an organometallic compound of the formula (II)

$$R_{2-n}MgX_n \qquad (II),$$

wherein n is 0 or 1, X is a halogen atom and R is a hydrocarbon group of 1 to 10 carbon atoms which may include a functional group having no influence on the reaction, in an ether solvent or in a non-aqueous mixture of ether solvent and a hydrocarbon, at a temperature range of −40° to 250° C., reacting said mixture at a temperature of not less than 25° C. to prepare a pentafluorophenyl magnesium compound of the formula (III)

$$(C_6F_5)_{2-n}MgX_n \qquad (III),$$

wherein n is 0 or 1, and X is a halogen atom, reacting the pentafluorophenyl magnesium compound of the formula (III) with a boron compound of the formula (IV)

$$BX_3 \qquad (IV),$$

wherein X is a halogen atom, or a substituent of formula (V)

$$OR \qquad (V),$$

wherein R is a hydrocarbon group of 1 to 10 carbon atoms which may also include a functional group having no influence on the reaction, or a substituent of formula (VI)

$$NRR' \qquad (VI),$$

wherein R and R' are a hydrocarbon group of 1 to 20 carbon atoms, each of which may respectively include a functional group having no influence on the reaction, and where R and R' may combine with each other to form a ring, said boron compound forming a complex of 1:1 to an ether solvent, said boron compound and said pentafluoromagnesium compound being combined in a ratio of 1 equivalent of the boron compound to 2.1–3.9 equivalents of the pentafluorophenylmagnesium compound of formula (III), within a temperature range of 0° C. to 250° C., to produce a coordination complex of tris(pentafluorophenyl)borane of the formula (VII)

$$(C_6F_5)_3B \qquad (VII),$$

with the ether solvent, and eliminating the ether solvent complexed with said tris(pentafluorophenyl)borane.

2. The process of claim 1 wherein the ether solvent complexed with said tris(pentafluorophenyl)borane is eliminated by a direct or indirect eliminating method.

3. The process of claim 2 wherein the ether solvent is eliminated by a direct elimination process wherein the complex coordinating the ether solvent to tris(pentafluorophenyl)borane is evaporated with sublimation at 30° C. to 200° C. at or under 10 Torr.

4. The process of claim 2 wherein said ether solvent coordinated to tris(pentafluorophenyl)borane is eliminated by an indirect eliminating method wherein said solvent coordinated to tris(pentafluorophenyl)borane is reacted with not less than 1 equivalent of alkylaluminum to coordinate said solvent to the alkylaluminum, thereby eliminating the solvent.

5. The process of claim 2 wherein said ether solvent coordinated to tris(pentafluorophenyl)borane is eliminated by an indirect eliminating method wherein a hydrocarbon type solvent having a higher boiling point than said coordinated solvent is mixed therewith and, subsequently, the hydrocarbon solvent is distilled off, thereby eliminating the coordinated solvent azeotropically.

6. The process of claim 3, wherein after elimination of said complex, the tris(pentafluorophenyl)borane is further reacted with pentafluorophenyllithium to provide tetrakis (pentafluorophenyl)borate, and then mixed with a solution of N, N-dimethylanilinium to provide N, N-dimethylanilinium tetrakis (pentafluorophenyl)borate.

* * * * *